United States Patent [19]

Risau et al.

[11] Patent Number: 5,286,716

[45] Date of Patent: Feb. 15, 1994

[54] INHIBITOR OF THE PROLIFERATION OF ENDOTHELIAL CELLS

[75] Inventors: Werner Risau, Gräfelfing; Hannes Drexler, Munich, both of Fed. Rep. of Germany

[73] Assignee: Max Planck Gesellschaft Zur Forderung Der Wissenschaften E.V., Gottingen, Fed. Rep. of Germany

[21] Appl. No.: 920,467

[22] PCT Filed: Mar. 1, 1991

[86] PCT No.: PCT/EP91/00388

§ 371 Date: Aug. 25, 1992

§ 102(e) Date: Aug. 25, 1992

[87] PCT Pub. No.: WO91/13094

PCT Pub. Date: Sep. 5, 1991

[30] Foreign Application Priority Data

Mar. 2, 1990 [DE] Fed. Rep. of Germany ....... 4006609

[51] Int. Cl.⁵ .............................................. A61K 37/00
[52] U.S. Cl. ..................................... 514/21; 530/350; 530/413; 530/416; 530/420
[58] Field of Search ............... 530/350, 413, 416, 420; 514/21; 435/240.25

[56] References Cited

U.S. PATENT DOCUMENTS 4,210,719 7/1980 Tolbert et al. ................. 435/240.25
4,229,531 10/1980 Tolbert et al. ................. 435/240.25

*Primary Examiner*—Michael G. Withyshyn
*Assistant Examiner*—C. Sayala
*Attorney, Agent, or Firm*—Nikaido, Marmelstein, Murray & Oram

[57] ABSTRACT

Protein which acts as an inhibitor of the proliferation of endothelial cells which is obtainable from baby hamster kidney cells (ATCC CCL 10) and has a molecular weight between 60 and 100 kD in gel filtration under native conditions and is thermally stable at 60° C., as well as a process for its isolation and its use in the treatment of diseases.

11 Claims, No Drawings

INHIBITOR OF THE PROLIFERATION OF ENDOTHELIAL CELLS

DESCRIPTION

The formation of new capillary vessels (angiogenesis) proceeds in an ordered series of steps: at a point at which a new vascular bud begins to grow out (usually in the region of post-capillary venules) the endothelial cells locally degrade the basal membrane, migrate towards the source of the factor stimulating angiogenesis, grow and divide, form a vessel lumen and land on other vascular buds or existing capillaries so that a new capillary section forms which finally surrounds itself with a newly formed basal membrane.

The angiogenic activity is usually almost completely inhibited in adult individuals. More intense angiogenic processes only occur in wound healing and in females in connection with the ovarian cycle. However, the turnover rate of the endothelial cells in the organism is generally low. The complete renewal of an existing endothelial cell population takes years, there are however, substantial organ and tissue-specific differences (Folkman, Medicine 29 (1985), 10–36).

The usual strict control of angiogenesis is abolished in the growth of solid tumours. A strong angiogenesis is absolutely necessary for the growth of tumours with a diameter of over 1 to 2 mm. Avascular tumours remain limited to a very small size due to the limited diffusion of the supply of gases and nutrients and with the removal of waste products. This deficiency in the capability of solid tumours to grow to a clinically significant size or to form metastases in the absence of a successful induction of angiogenesis has caused a great interest in research into compounds which inhibit angiogenesis.

The commercial application of such inhibitors is for the inhibition of tumour growth in general, in particular for the inhibition of tumours based on endothelial cells such as Kaposi sarcoma and haemangiomas. In addition a therapeutic use for other diseases is also possible which are due to excessive capillary growth. Particular examples of this are diabetic retinopathy and retrolental fibroplasia, both of which are eye diseases. A further use is in the treatment of wounds in which an inhibitor of angiogenesis can be used to regulate wound healing i.e. in delaying the regeneration of blood vessels. In addition an angiogenesis inhibitor can also be used for the treatment of rheumatoid arthritis. In this disease a vascularization of cartilage is observed (as generally seen in every inflammation in this region) which can be suppressed by an angiogenesis inhibitor.

A series of extracts which inhibit angiogenesis have been prepared from avascular tissues (see D'Amore and Braunhut, in Edothelial Cells, Vol. II, edited by U.S. Ryan, CRC Press, Boca Raton, Fla., 13–37). Anti-inflammatory agents also suppress angiogenesis (Robin et al., Arch Ophthamol. 103 (1985), 284–287; Polverini and Novak, Biochem. Biophys. Res. Comm. 140 (1986), 901–907) such as e.g. protamine (Taylor and Folkman, Nature 297 (1982), 307–312) angiostatic steroids (Crum et al., Science 230 (1985), 1375–1378), a placental RNAse inhibitor (Shapiro and Vallee, Proc. Natl. Acad. Sci. USA 84 (1987), 2238–2241) and a series of compounds which influence matrix synthesis and stability (see e.g. Ingber and Folkman, Lab. Invest. 59 (1988), 44–51). For some of these inhibitors an inhibition of tumour growth or regression was observed in vivo but not with all tumours. Furthermore the toxicity of these angiogenesis inhibitors also remains a problem.

An angiogenesis inhibitor was found by Rastinejad et al. (Cell 56 (1989), 345-355) in a medium with hamster cells and hamster-human hybrid cells which suppresses the neovascularization in vivo. This compound is apparently a glycoprotein with a molecular weight of 140 kD. However, this inhibitor only has a low stability and in particular it is not thermally stable.

It was therefore the object of the present invention to provide a more stable angiogenesis inhibitor which can hence be more readily used therapeutically.

The object according to the present invention is achieved by a protein which acts as an inhibitor of the proliferation of endothelial cells which is obtainable from baby hamster kidney cells (ATCC CCL 10) which has a molecular weight of ca. 60 to 100 kD in gel filtration under native conditions and has a high thermal stability.

The inhibitor according to the present invention is a protein since its inhibitory action on endothelial cell proliferation is completely destroyed on digestion with trypsin and chymotrypsin. The inhibitor is thermally stable since even after a 45 minute heat treatment at 60° C. is still has at least 50 % of its original activity. Its molecular weight in a native form was shown by gel filtration experiments. A further feature of the protein according to the present invention is that it does not bind to heparin-sepharose and can be separated in this way from growth factors for endothelial cells which bind to heparin.

The inhibitory activity was measured in the BAE proliferation test. For this endothelial cells from the bovine aorta (BAEC = bovine aortic endothelial cells) were used in a modified proliferation test in order to determine the activity of the inhibitor.

The present invention in addition concerns a process for isolating the protein according to the present invention from baby hamster kidney cells (ATCC CCL 10). The culture of the cells was carried out in a growth medium with addition of foetal calf serum until a considerably confluent sheet of cells is obtained. Subsequently the culture medium is conditioned in serum-free medium for preferably 2 to 3 weeks until an increased detachment of the cell sheet from the vessel walls is observed. Then the baby hamster kidney cells (BHK) are completely detached by protease treatment, preferably by trypsin/EDTA treatment, and individual cells are resuspended and again cultured until confluent.

The first step in the isolation of the inhibitor from BHK conditioned medium is preferably an ultrafiltration in which an ultrafiltration membrane with a nominal exclusion limit of 10 kD is used. In this step the filtrate is discarded and the proteins in the retentate are subsequently subjected to an ammonium sulphate precipitation.

For this ammonium sulphate is added up to ca. 75% saturation whereby the protein according to the present invention is located in the precipitate. The precipitate is isolated by centrifugation, resuspended and dialyzed against a suitable buffer.

The presence of an inhibitor of endothelial cell proliferation in the medium conditioned by BHK cells can already be detected in the BAE test after a 10-fold concentration of the medium. The total inhibitory activity in the medium can be precipitated by the ammonium sulphate precipitation at 75% saturation.

If desired, a subsequent purification step by affinity chromatography on heparin-sepharose can be carried out. This serves to separate angiogenesis activators or inhibitors which bind to heparin. The proteins which do not bind to the column are used for further purification.

An anion-exchange chromatography on Q-sepharose is preferably carried out as the next step in the further purification. The protein according to the present invention binds to the anion-exchange column and can be eluted with a 0 to 1 mol/l NaCl salt gradient in a suitable buffer, preferably 50 mmol/l Tris-HCl, pH 7.5.

Under the conditions described the inhibitor is eluted from the column at a NaCl concentration of between 0.24 and 0.32M.

As an alternative to the aforementioned conventional chromatography with Q-sepharose, this step can also be carried out by an FPLC on a MonoQ 10/10 column (Pharmacia/LKB; Freiburg).

Fractions of the anion-exchange chromatography which contain the inhibitory activity are pooled and concentrated up to 40-fold by ultrafiltration. The concentrated sample can subsequently be applied to a gel filtration column, preferably TSK HW 55s (Merck, Darmstadt) and the bound protein can again be removed from the column with PBS as eluting agent.

The gel filtration on TSK HW 55s material did not result in any additional purification effect but enabled the molecular weight of the inhibitor to be determined as being about 60 kDa. Gel filtrations performed simultaneously to this under the same buffer conditions by means of FPLC on a Superose 12 column (Pharmacia/LKB; Freiburg) led to the same result.

Bovine serum albumin (BSA) which contaminated fractions with inhibitor activity after this gel filtration could be removed by subsequent chromatography on Affi-gel blue (beaded, crosslinked agarose gel with covalently attached Cibacron Blue F3GA dye) since most of the inhibitor is not bound by this material. This step can also directly follow the heparin-sepharose chromatography or the ion-exchange step.

Subsequently a hydrophobic interaction chromatography is carried out on a HPLC apparatus, preferably on a HIC spherogel CAA column 100×4.6 mm (Beckman Instruments, Munich). The sample is applied with a high ammonium sulphate concentration, preferably 3 mol/l. The bound substances are eluted with a linear reversed salt gradient. In order to demonstrate the inhibitory activity after this step the fractions have to be dialysed after elution against 20 mmol/l Tris-HCl, pH 7.5.

This step is a further effective method of concentrating the inhibitor and at the same time to remove contaminating proteins. The inhibitor binds to the matrix under the selected conditions and is eluted from the column 21 to 23 minutes after the start of the gradient.

The final product obtained according to the process according to the present invention still contains small amounts of foreign proteins. However, a pure product can be isolated by a further purification step for which it is possible to determine an amino acid partial sequence. In turn DNA oligonucleotide probes can be prepared from this and consequently a total amino acid sequencing of the inhibitor can be carried out via the cDNA or genomic DNA. These methods are known to a person skilled in the area of molecular biology.

Neonatal tissue, preferably baby hamster kidney cells (ATCC CCL 10) can be used as the starting material for the isolation of the protein according to the present invention since the neonatal tissue presumably contains much higher concentrations of the inhibitor than the tissue from adult organisms although it is doubtful whether adult organisms contain this inhibitor at all.

In addition the present invention concerns a pharmaceutical agent which contains the protein according to the present invention as the active substance as well as the usual filling, carrier or/and auxiliary substances.

The protein according to the present invention can be used in the treatment of all diseases in which an increased angiogenesis occurs and which have already been mentioned above. In particular the protein according to the present invention can be used to inhibit tumour growth such as of Kaposi sarcomas or haemangiomas, for the treatment of eye diseases in which an increased capillary growth occurs, in particular in diabetic retinopathy and retrolental fibroplasia, as well as in rheumatoid arthritis or in order to regulate wound healing.

The preferred dose of the protein according to the present invention should be on a scale of µg to a maximum of mg per kg body weight.

It is intended to elucidate the invention further by the following examples.

EXAMPLES 1

Cell culture

Cells of the BHK-21 (ATCC CCL 10) type were used to prepare the conditioned medium (passage 150–159).

Culture of the cells

BHK cells were first inoculated in DMEM/F12 medium (1:1; GIBCO, Paisley, Scotland) supplemented with 5% foetal calf serum (FCS, Boehringer Mannheim) in Costar cell culture flasks with a growth area of 75 cm$^2$ and incubated in an incubator at 37° C., 7% $CO_2$ and 95% humidity until the cells became confluent.

After confluence is achieved the cells were detached by trypsin/EDTA treatment, taken up in DMEM/F12 medium, centrifuged (Häreus, 5 minutes at 1000 rpm), resuspended in DMEM/F12 medium and transferred to Costar cell culture flasks with 165 cm$^2$ growth area. The incubation of the cells until confluence was achieved was carried out under the same conditions as stated above.

The cells of a cell culture flask with 165 cm$^2$ growth area were then detached by again treating with trypsin/EDTA, resuspended in 50 ml DMEM/F12 medium, 5% FCS, 10 mM HEPES pH 7.5 and transferred to cell culture roller flasks with a growth area of 900 cm$^2$ (Costar). The roller flasks were either used uncoated or after coating with gelatin. The culture as well as the conditioning of the culture medium (see below) of the cells transferred to the roller flasks was carried out on a roller system (1.5 rpm) and in a Vismara incubator from the Tecnomara company at 37° C. without aeration with carbon dioxide. The conditioning of the culture medium of the BHK cells was only started after the cells in the roller flasks had formed a cell sheet which was substantially confluent. Up to then the culture medium (DMEM/F12, 5% FCS, 10 mmol/l HEPES pH 7.5) was replaced every 3 days.

Conditioning of the culture medium

The BHK cells of a roller flask were washed in 50 ml serum-free medium (DMEM/F12, 10 mmol/l HEPES pH 7.5) for 4 to 6 hours, the washing solution was discarded and 200 ml medium was added. The conditioning of the culture medium with 200 ml serum-free medium in each case was carried out for 72 hours at 37° C. and 1.5 rpm for 2 to 3 weeks until an increased detachment of the cell sheet from the vessel walls was observed.

At this time the BHK cells were completely detached from the vessel walls by trypsin/EDTA treatment and separated, then resuspended in 100 ml DMEM/F12, 5% FCS and 10 mM HEPES and dispensed in equal portions into 2 roller flasks where they were cultured as described under 1.1.1. until they again reached confluence.

The conditioned medium was freed of detached cells by centrifugation and stored at 4° C. after sterile filtration.

EXAMPLE 2

Isolation of the inhibitor from BHK-conditioned medium

2.1 Concentration of the conditioned medium

2.1.1. Ultrafiltration 4 to 6 liters of the conditioned medium was concentrated to a tenth of its original volume with the aid of a Minitan ultrafiltration system (Millipore GmbH, Eschborn). Membranes of the PGLC type made of regenerated cellulose (Millipore GmbH, Eschborn) with a nominal exclusion limit of 10 kDa were used as ultrafiltration membranes. The filtrate was discarded and the proteins in the retentate were subjected to an ammonium sulphate precipitation.

2.1.2. Ammonium sulphate precipitation

In order to further concentrate the conditioned medium after adjusting the pH value to 6.5, solid ammonium sulphate (232.2 g/l; 75% saturation) was added in small portions to the retentate of the ultrafiltration while stirring continuously and the proteins were precipitated overnight. The precipitate was isolated by centrifugation for 30 minutes at 20000 g, dissolved in 100 to 150 ml cold distilled water and dialysed against 3×5 l PBS, pH 7.5 (nominal exclusion limit of the Visking dialysis tubes: 12 to 14 kDa; Roth company). Smaller precipitates which formed during the dialysis were removed by centrifugation before the next purification step.

2.2 Affinity chromatography on heparin sepharose

Heparin-sepharose (Pharmacia/LKB, Freiburg) in a 1×5 cm column was equilibrated with PBS (flow rate: 40 ml/hour) and the material dialysed against PBS was applied to the column at the same flow rate. The proteins which do not bind to the column were used for the further purification.

2.3 Anion-exchange chromatography on Q-sepharose

The material which was not bound to the heparin sepharose was diluted to three times the volume with 50 mmol/l Tris/HCl buffer, pH 7.5 and pumped at 250 ml/hour onto a column packed with Q-sepharose fast flow (Pharmacia/LKB; Freiburg) (equilibrated in 50 mmol/l Tris/HCl buffer, pH 7.5). After washing the column with the application buffer, the bound proteins were eluted with a linear salt gradient (total volume: 1600 ml) from 0 to 1 mol/l NaCl in 50 mmol/l Tris/HCl, pH 7.5.

1 2.4 Gel filtration chromatography with TSK HW55s

Fractions of the anion-exchange chromatography which contained the inhibitory activity (see example 3, BAE test) were pooled and concentrated 40-fold in an Amicon ultrafiltration chamber (PM10 ultrafiltration membrane from Amicon).

The concentrated sample was subsequently applied to a TSK HW55s column (Merck, Darmstadt; 1.5×70 cm) equilibrated in PBS and the chromatography was carried out with PBS as the eluant at a flow rate of 20 ml/hour.

2.5 Removal of BSA by chromatography on Affi-gel blue

Active fractions from step 2.4 were pooled, diluted with the same volume of 20 mmol/l sodium phosphate buffer, pH 6.8 and applied to an Affi-gel blue (beaded, crosslinked agarose gel with covalently attached Cibacron Blue F3GA dye) column (50 to 100 mesh; BioRad; 1.5×12 cm) equilibrated with the same buffer at a flow rate of 40 ml/hour. The unbound material which was almost completely free of BSA was used further in the next step.

2.6 Hydrophobic interaction chromatography on HIC spherogel CAA

This step was carried out on a HPLC apparatus of the Kontron Company, Eching.

4 ml aliquots of the unbound material from step 2.5 were concentrated to 150 to 200 µl over Centricon 10—or Centricon 30—microconcentrators (Amicon) and applied to a HIC spherogel CAA column (100×4.6 mm; Beckmann Instruments, Munich) at an ammonium sulphate concentration of 3 mol/l (50 mmol/l sodium phosphate, pH 6.8 as the buffer). The elution of the bound substances is carried out with a linear reversed salt gradient of 3 mol/l ammonium sulphate/50 mmol/l sodium phosphate, pH 6.8 after 50 mmol/l sodium phosphate/1 mmol/l sodium acetate, pH 6.8 in 35 minutes.

In order to detect the inhibitory activity in the BAE test (see item 1.3) the fractions had to be dialysed against 20 mmol/l Tris/HCl, pH 7.5.

EXAMPLE 3

Detection of the inhibitor in the BAE proliferation test

Endothelial cells from the bovine aorta (BAEC=bovine aortic endothelial cells) were used in a modified proliferation test to identify the endothelial cell inhibitor. For this, 6000 to 9000 BAEC's in DMEM, 5% FCS were inoculated per well of a Costar multiculture plate (24 wells per plate) and incubated overnight in an incubator at 37° C./7% carbon dioxide content. On the next day the non-adherent cells were removed by a change of medium (DMEM/5% FCS and 0.02 ml FGF from bovine retinae/ml medium). (The endothelial cells receive a mitogenic stimulus by the addition of FGF to the culture medium which stimulates their proliferation by 1.5 to 3-fold compared to the control value).

Up to 0.04 ml of each fraction that was to be tested for the presence of the inhibitor was pipetted into 2 wells of the culture plate in each case (duplicate determination) and the cell counts were determined by a Coulter counter after 72 hours incubation in an incubator.

4. Characterization of the inhibitor

4.1 Thermal stability

Inhibitory active fractions were incubated for 10 minutes or 45 minutes at 60° C., then sterile filtered and examined in the BAE test for activity which was still present.

4.2 Protease sensitivity 0.1 ml of an inhibitory fraction was incubated at 37° C. in 20 mM Tris/HCl buffer, pH 7.5 for 90 minutes with 0.05 mg trypsin (Sigma) or chymotrypsin A4 (Boehringer). The digestion was subsequently stopped by addition of aprotinin (Sigma), the samples were sterile filtered and examined in the BAE test.

The deposited cell line ATCC CCL 10 was deposited on 10th Jun. 1965 at the American Type Culture Collection, 12301 Parklawn Drive, Rockville, Md. 20852-1776, USA under the number stated above.

We claim:

1. A protein purified from baby hamster kidney cells which has a molecular weight between 60 and 100 kD as determined by gel filtration under native conditions and is thermally stable at 60° C., wherein said protein inhibits the proliferation of endothelial cells and is obtained by a process comprising the steps of:
   a) concentrating a conditioned medium of embryonic cells by ultrafiltration,
   b) precipitating the protein using ammonium sulfate, and
   c) purifying the protein further using affinity chromatography on heparin sepharose, anion-exchange chromatography, Affi-gel chromatography and/or hydrophobic interaction chromatography.

2. The protein according to claim 1 wherein the baby hamster kidney cells are from cell line ATCC CCL10.

3. The protein according to claim 1 wherein said protein retains about 70% of the original activity after treatment at 60° C. for 45 minutes.

4. The protein according to claim 1 wherein said protein does not bind to heparin-sepharose.

5. A protein purified from baby hamster kidney cells which has a molecular weight between 60 and 100 kD as determined by gel filtration under native conditions and is thermally stable at 60° C., wherein said protein inhibits the proliferation of endothelial cells and does not bind to heparin sepharose.

6. A process for isolating a protein purified from baby hamster kidney cells which has a molecular weight between 60 and 100 kD as determined by gel filtration under native conditions and is thermally stable at 60° C., wherein said protein inhibits the proliferation of endothelial cells, comprising the steps of:
   a) concentrating a conditioned medium of embryonic cells,
   b) precipitating the protein using ammonium sulfate, and
   c) purifying the protein further using chromatography.

7. The process according to claim 6 wherein said embryonic cells are baby hamster kidney cells from cell line ATCC CCL10.

8. The process according to claim 6 wherein ultrafiltration is used in step a) with a membrane that has a nominal exclusion size of 10 kD and in step b) ammonium sulfate is added up to about 75% saturation.

9. The process according to claim 6 wherein said chromatography includes anion exchange and hydrophobic interaction chromatography.

10. The process according to claim 6 wherein said chromatography includes heparin affinity chromatography, gel filtration chromatography and/or Affi-gel chromatography.

11. A pharmaceutical composition comprising a protein purified from baby hamster kidney cells which has a molecular weight between 60 and 100 kD as determined by gel filtration under native conditions and is thermally stable at 60° C., wherein said protein inhibits the proliferation of endothelial cells, in combination with a suitable carrier.

* * * * *